United States Patent
Markowitz et al.

(10) Patent No.: US 6,238,429 B1
(45) Date of Patent: *May 29, 2001

(54) BIOLOGIC CABLING

(75) Inventors: H. Toby Markowitz, Roseville; Maura G. Donovan, St. Paul; Khawar Mehdi, Minneapolis, all of MN (US)

(73) Assignee: Medtronic, Inc., Minneapolis, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/072,819

(22) Filed: May 5, 1998

Related U.S. Application Data

(60) Provisional application No. 60/045,638, filed on May 5, 1997.

(51) Int. Cl.$^7$ ..................................................... A61N 1/05
(52) U.S. Cl. ............................. 607/116; 607/2; 128/898; 424/569
(58) Field of Search .................................... 607/1–3, 115, 607/116, 119; 623/12, 14, 25; 606/153, 158; 424/422, 423, 93.1, 93.2, 93.7, 569; 128/898

(56) References Cited

U.S. PATENT DOCUMENTS

| | | | |
|---|---|---|---|
| 5,562,946 | 10/1996 | Fofonoff et al. | 427/2.12 |
| 5,602,301 | 2/1997 | Field | 800/2 |
| 5,709,934 | 1/1998 | Bell et al. | 428/305.5 |
| 5,834,029 | * 11/1998 | Bellamkonda et al. | 424/570 |
| 5,869,041 | * 2/1999 | Vandenburgh | 424/93.21 |
| 5,919,449 | * 7/1999 | Dinsmore | 424/569 X |

OTHER PUBLICATIONS

Strategies for Mycardial Repair (Journal of Interventional Cardiology vol. 8 No. 4 1995 pp387–393) Gou Young Koh et al.

Long–Term Survival of AT–1 Cardiomyocyte Grafts in Syngeneic Mycardium (Rapid Communication pp H1727–H 1733) Gou Young Koh et al.

Stable Fetal Cardiomyocyte Grafts in the Hearts of Dystrophic Mice and Dogs (The American Society of Clinical Investigation Inc. vol. 96 Oct. 1995 pp 2034–2042) Gou Young Koh et al.

Fixing the Failing Heart (Circulation vol. 95, No. 4 Feb. 18, 1997 pp771–772) Claude Lenfant MD.

Genetically Selected Cardiomyocytes from Differentiating Embryonic Sten Cells Form Stable Intracardiac Grafts (The American Society for Clinical Investigation Inc. vol 98, No. 1 Jul. 1996 pp216–224) Michael G. Klug et al.

DNA Synthesis and Multicucleation in Embryonic Stem Cell–Derived Cardiomyocytes (The American Physiological Society pp–H1913–H1921) Michael G. Klug et al.

Restoration of B–Adrenergic Signaling in Failing Cardiac Ventricular Myocytes Via Adenoviral–Mediated Gene Transfer (The Nat'l Academy of Sciences vol. 94 p 12100–12105 Shahab A. Akhter et al.

Transfection of Rhabdomyosarcoma Cells with Connexin43 Induces Myogenic Differentiation (Cell Growth & Differentiation vol. 8 pp 533–540 May 1997) A.A. Proulx et al.

(List continued on next page.)

*Primary Examiner*—Jeffrey R. Jastrzaf
(74) *Attorney, Agent, or Firm*—Michael B. Atlass; Harold R. Patton

(57) ABSTRACT

A length of living conductive cells may be injected directly or may be grown to be attached to a fibrous matrix of material that provides for flexible structure so as to deliver a stimulation signal from one end of the biologic cable to the other to induce a physiologic reaction in body tissue.

17 Claims, 9 Drawing Sheets

OTHER PUBLICATIONS

Disturbed Connexin43 Gap Junction Distribution Correlates with the Location of Reentrant Circuits in the Epicardial Border Zone of Healing Canine Infarcts That Cause Ventricular Tachycardia (circulation vol. 95, pp 987–996) N.S. Peters et al.

Characterization of Gap Junction Channels in Adult Rabbit Atrial ANC Ventricular Myocardium (Circulation vol. No. 5 pp673–681) Sander Verheule et al).

Hybrid Muscular Tissues Prepartion of Skeletal Muscle Cell–Incorporated Collagen Gels (Cell Transplantation vol. 6, No. 2 1997 pp–109–118) takahisa Okano et al.

Tissue Engineering of Skeletal Muscle Highly Dense, Highly Oriented Hybrid Muscular Tissues Biomimicking Native Tissues (Vascular Cell Biology Lab pp–M749–M753.

Formation of Nascent Intercalated Disks Between Grafted Fetal Cardiomyocytes and Host Myocardium (Science vol. 261 Apr. 4, 1994 PP–97–101) M. Soonpaa et al.

Targeted Expression of Transforming Growth Factor B1 in Intracardiac Grafts Promotes Vascular Endothelial Cell DNA Synthesis (The Journal of Clinical Investigation Inc. vol. 95, Jan. 1995 pp–114–121) Gou Young Koh.

Hybrid Muscular Tissues:Preparation of Skeletal Muscle Cell_Incorporated Collagen Gels (Cell transplatation Volume p Nov. 2, 1997) Takahisa Okano et al.

* cited by examiner

BIOLOGIC CABLING

This application is a conversion of Provisional Application No. 60/045,638, filed on the fifth of May of 1997 which is incorporated herein by reference.

This invention is related to cardiac interventional systems and devices and may provide numerous therapies and device applications which are heretofore unknown. with the development of biologic cabling many new devices and therapies become possible where conduction of a physiologically active signal to one part of the body is needed.

BACKGROUND

Much interest has been generated in the scientific, engineering and medical communities regarding the adaptation of living cells to perform additional functions. There has been some work of Dr. Loren Field of Indianapolis in which cardiomyocetes have been modified to repair or replace heart tissue. While it has been demonstrated that small patches of cardiac or other muscular tissue can be grown and suggested that such patches can be placed within or on particular organs, including the heart, the development of a specific and novel form of cellular structure, not found in nature, has not been described to the knowledge of this inventor. This structure which we will call "Biologic Cabling" is not an organism but a building block for alternative tissue pathways for electrical signal conduction throughout a living body.

Already, there are banks of stem cells and other cells are now available which can be used to develop particular tissues for various uses, but no one has provided a structure well suited to conducting electrical activity throughout a living body comprised primarily or exclusively of living cells.

It should be noted that by using the most biologically friendly materials, living cells themselves, many of the present problems with implantable device/body interface issues are negated. For example, in the pacemaker area, it is not advisable to attach anything to the left ventricular internal wall or put it in that chamber because of the propensity of such additions to throw clots which can easily then be lodged in the brain.

It will become apparent to the reader that there are numerous applications for biologic cabling.

BRIEF DESCRIPTION OF THE DRAWINGS

Four figures are provided which show the experimental development of biologic cabling by providing particularized structures for the application of such modified cardiomyocetes to transfer the electrical impulses through directed pathways, or biologic cables so as to restructure the electrical timing of the heart depolarization.

SUMMARY OF THE INVENTION

It is an object of this invention to provide a method for building a structure of biologically active cells that can be implanted into or which may be grown at a given location within living tissue and once there, conduct electrical signals from one end of the structure to the other and to provide cables made of living cells that conduct biologically active signals to induce physiologic actions of cells at the receiving end of such cable devices.

In general one technique for performing an implant of a biologic cable will employ the technique known as Trans-Myocardial Regeneration (TMR)(which is a laser employing technique) or through needle insertion of the altered myocetes or stem cells.

The cable cells can be treated, that is genetically altered in vivo in place, or preferably delivered altered or selected to perform their conductive function before insertion. By forming an insulative of cells in a concentric mass around conductive cells we can insert a conduit with stem cells that will be conductive attached to its interior.

Such a structure can be supported by non-cellular, that is manufactured conduit material, such as for example, collagen.

The structure once placed can be used in many ways to stimulate any tissue its terminus can be affixed to.

Many devices can be built using such structures including but not limited to pacemakers with biologic cables for delivering very low energy pacing pulses to the heart, and for doing so without connection through a metal or other conventional conductor; means for transferring a depolarization wavefront from one part of a heart to another to short circuit accessory conductive pathways and avoid or correct arrhythmias, repair of blocked natural conduction pathways, creation of cellular pacemakers and so on.

DETAILED DESCRIPTION OF THE PREFERRED EMBODIMENTS

Incorporated herein in their respective entireties by this reference are all of the articles and patents cited throughout this application. This is done to avoid the unnecessary reiteration of what is already known in these arts.

Figure 1:
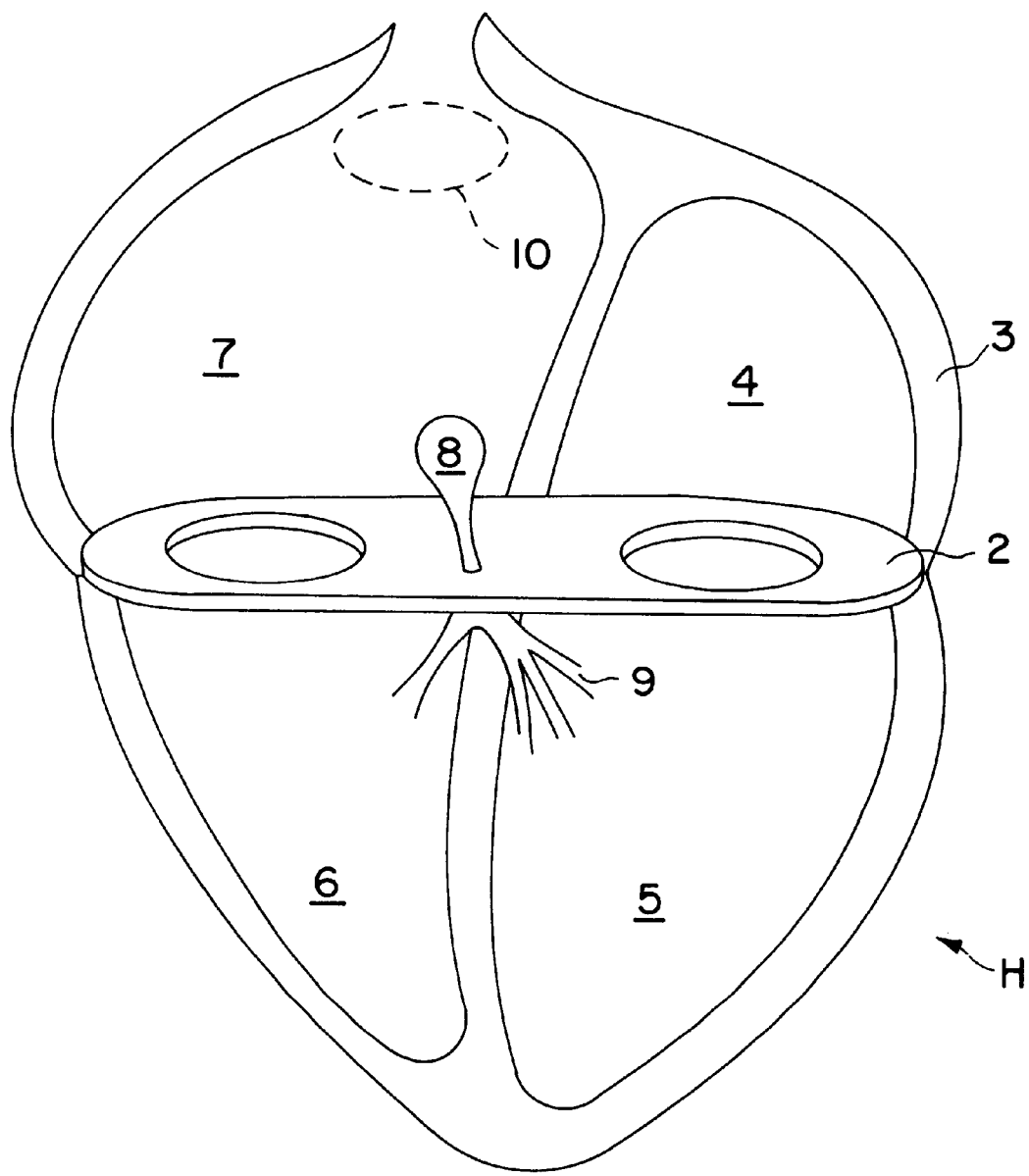
FIG. 1 is a heuristic view of the major structural aspects of a heart showing the conductive pathway of the AV node, HIS bundle and the starts of the Purkinje fibers.
Figure 2:
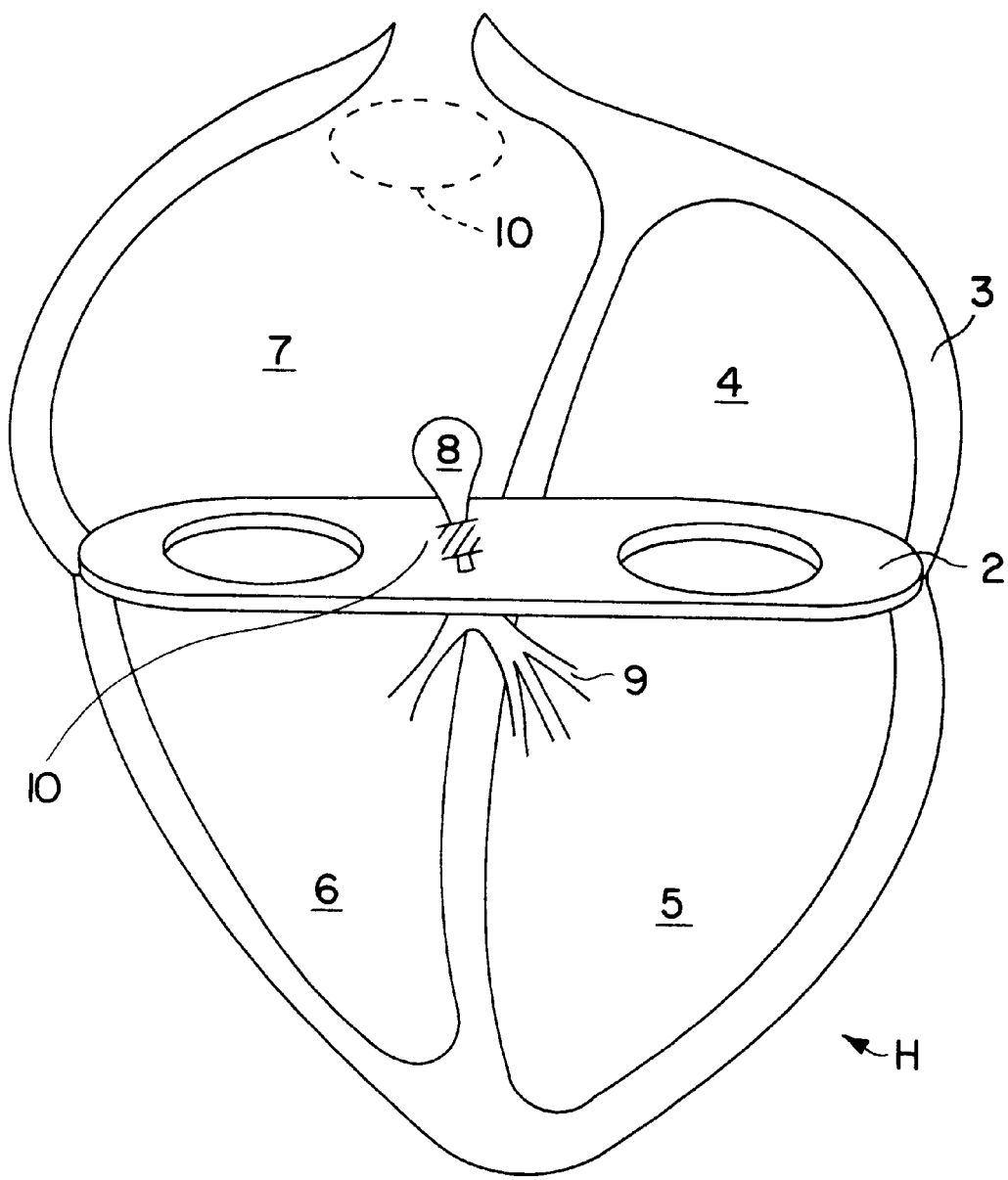
FIG. 2 illustrates the heart of FIG. 1 with the severance of the main pathway is shown.

Referring first to FIG. 1, a heart H is illustrated in a rudimentary form. The fibrous skeleton 2 is at the center of the heart, of course allowing for passage of blood from a left atrium 4 to a left ventricle 5 and from a right atrium 7 to a right ventricle 6. Only the outline 3 of the heart tissue is illustrated. SA node 7 initiates the electrical and contractual conduction sequence of the typical heart. When the conduction reaches the AV node 8, the electrically conductive fibers 9 transmit the impulse of contraction around the ventricular muscle tissue to produce a unified and powerful contraction. If as in FIG. 2, an ablation is made across the conductive pathway from the AV node to the Purkinje fibers, this normal conduction system will be ineffective and either accessory connective pathways directly from Atrial muscle to Ventricular muscle tissue will cause Ventricular contractions or the Ventricular muscle material will contract at its normal rate. This is generally understood to be ineffective for maintenance of life.

Figure 3:
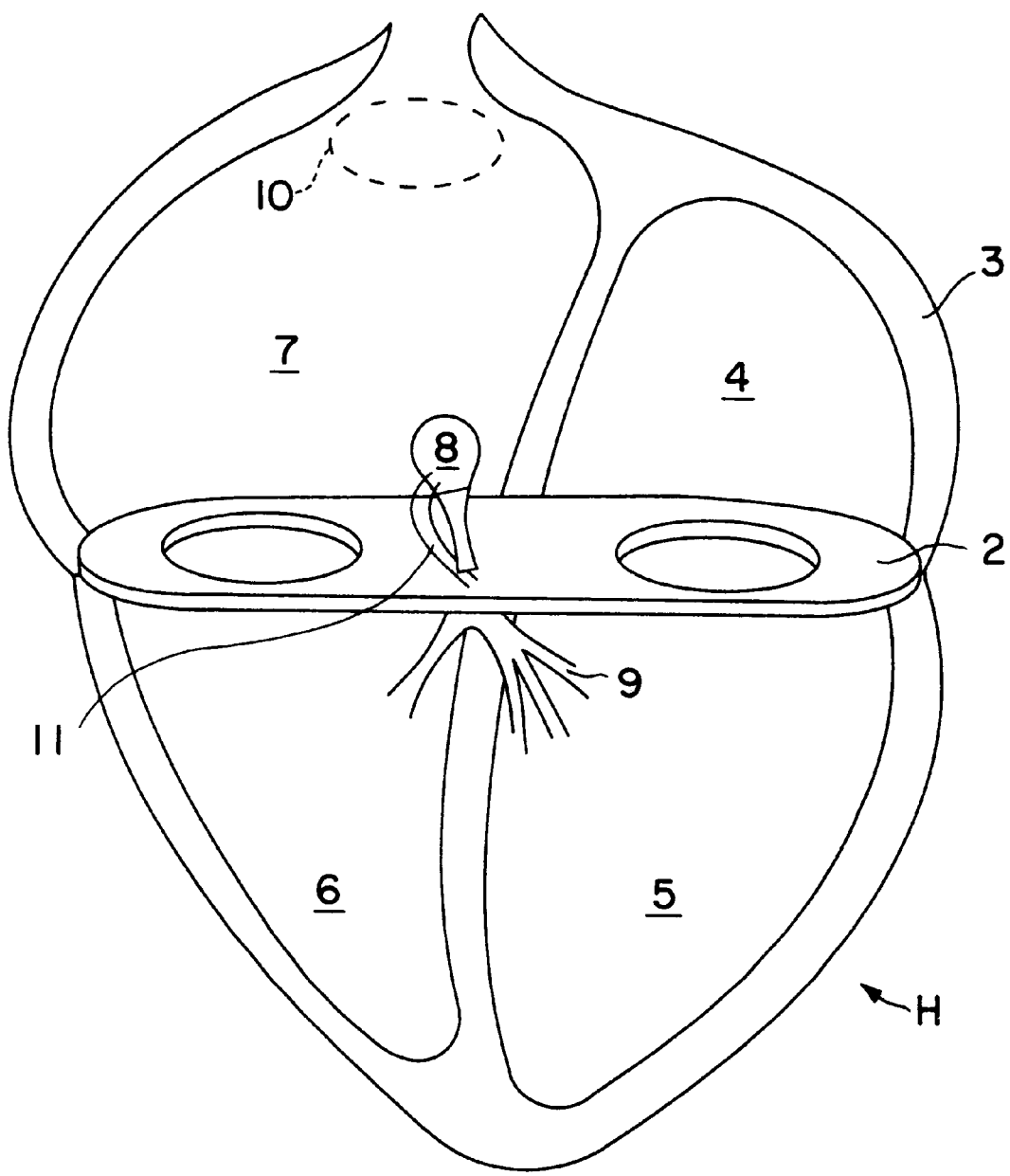
In FIGS. 3 and 4 are alternative views of repair of the heart of FIG. 1, showing the location of the placement of replacement biologic cables.
Figure 4:
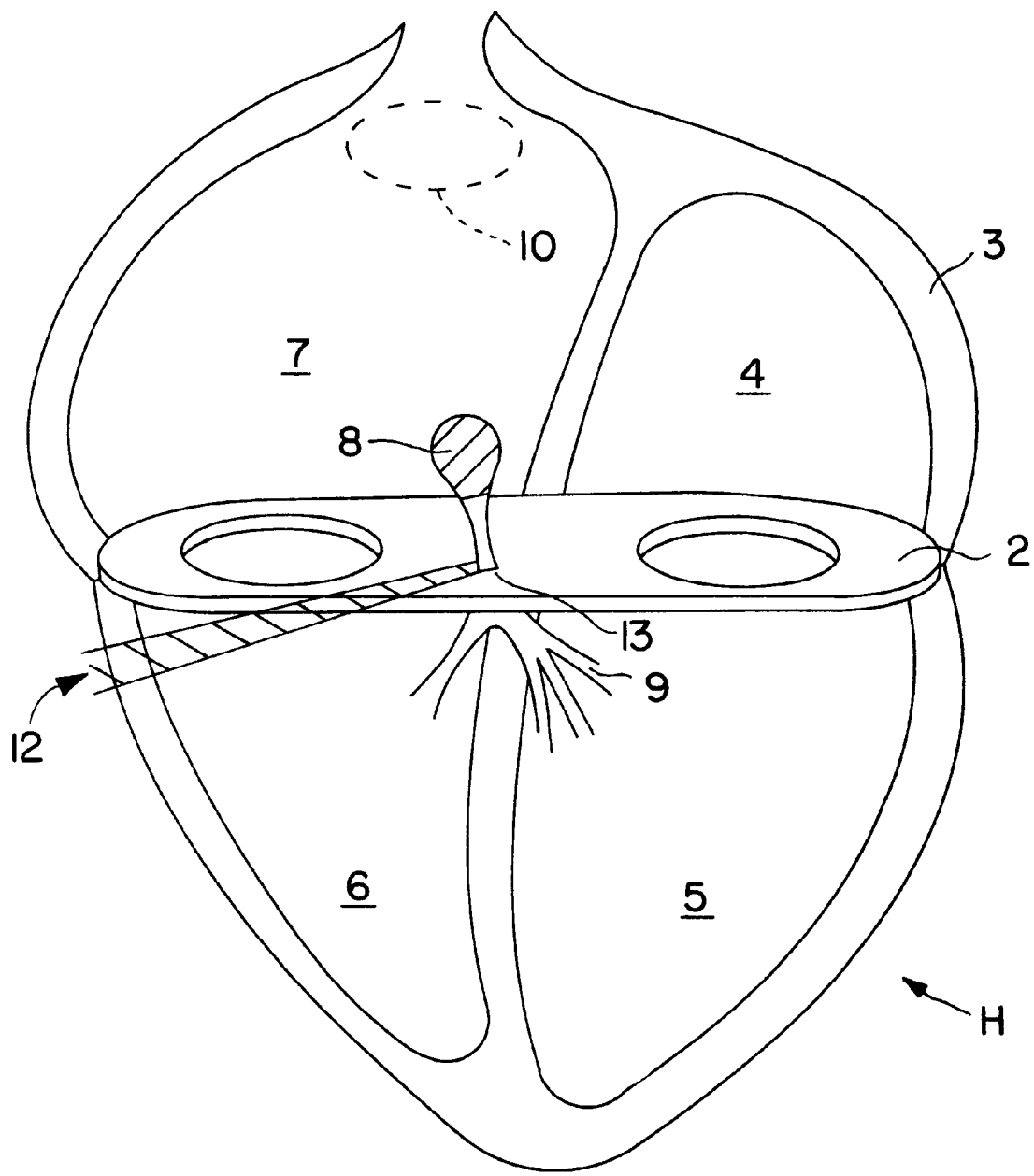

In FIG. 3, an area of dead tissue is illustrated between the AV node and the Purkinje fibers. In an optimal use of biologic cable for connecting a now disconnected AV node to the Purkinje fibers a stretch of biologic cable 11 is illustrated on this model of the heart. An alternative repair operation may be available as illustrated in FIG. 4. Here, the AV node remains isolated from the Purkinje fibers by the dead tissue. Nevertheless a pathway of biologic cable 12 has been inserted through the heart to connect with the remaining live head of the Purkinje fiber system 13, underneath the dead tissue.

Figure 8:
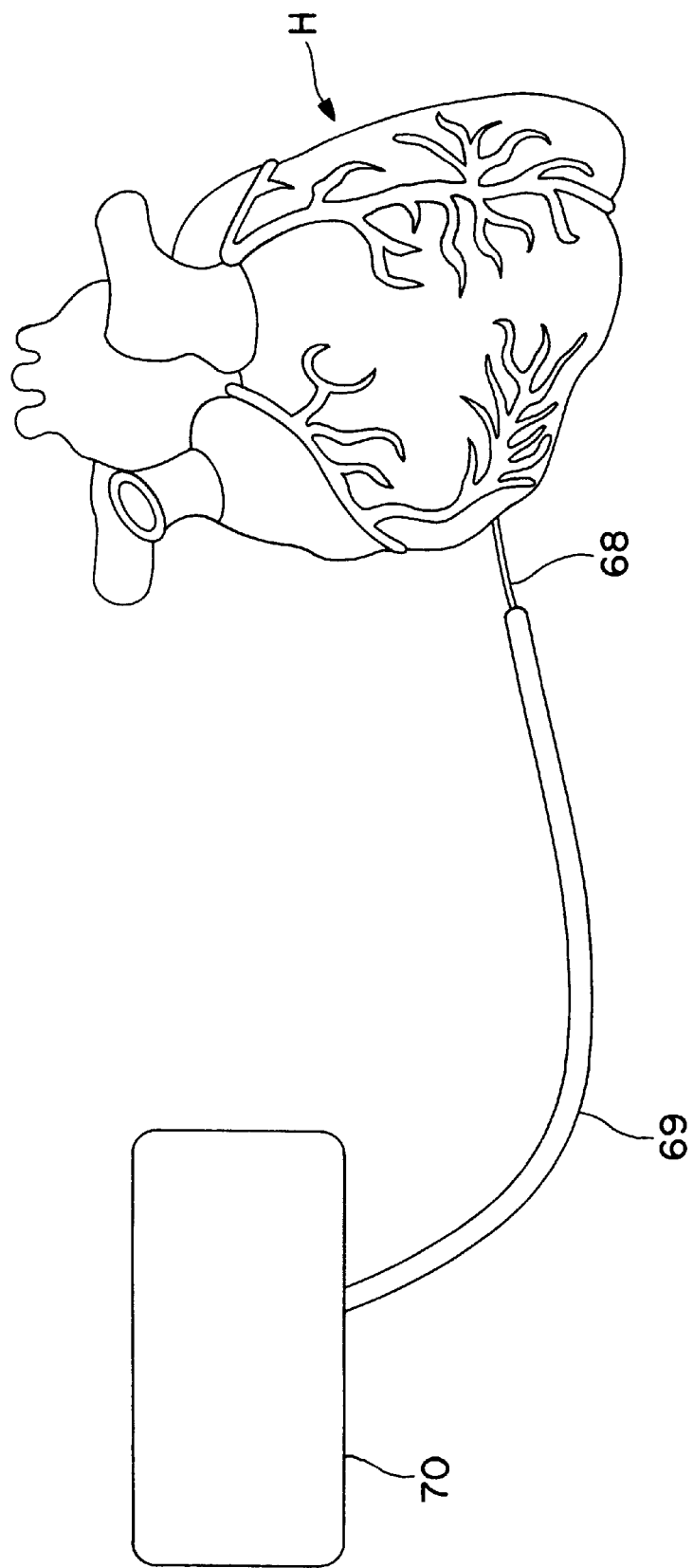
FIG. 8 is an illustration of a heart and implantable medical device connected thereto.

In either of these ways, the insertion of biologically active and electrically conductive cells will re-enable access to the heart's conduction system. In the FIG. 3 illustration, by taking advantage of an intact AV node, and in FIG. 4, by providing a pathway to an external site at which electrical stimulation can be delivered by more ordinary means, such as by a pacemaker. Such a system is illustrated in FIG. 8, with a pacemaker type implant 70 connected by a normal electrical cable 69 to the extension of a biologic cable 68, extending from the heart H.

Figure 5:
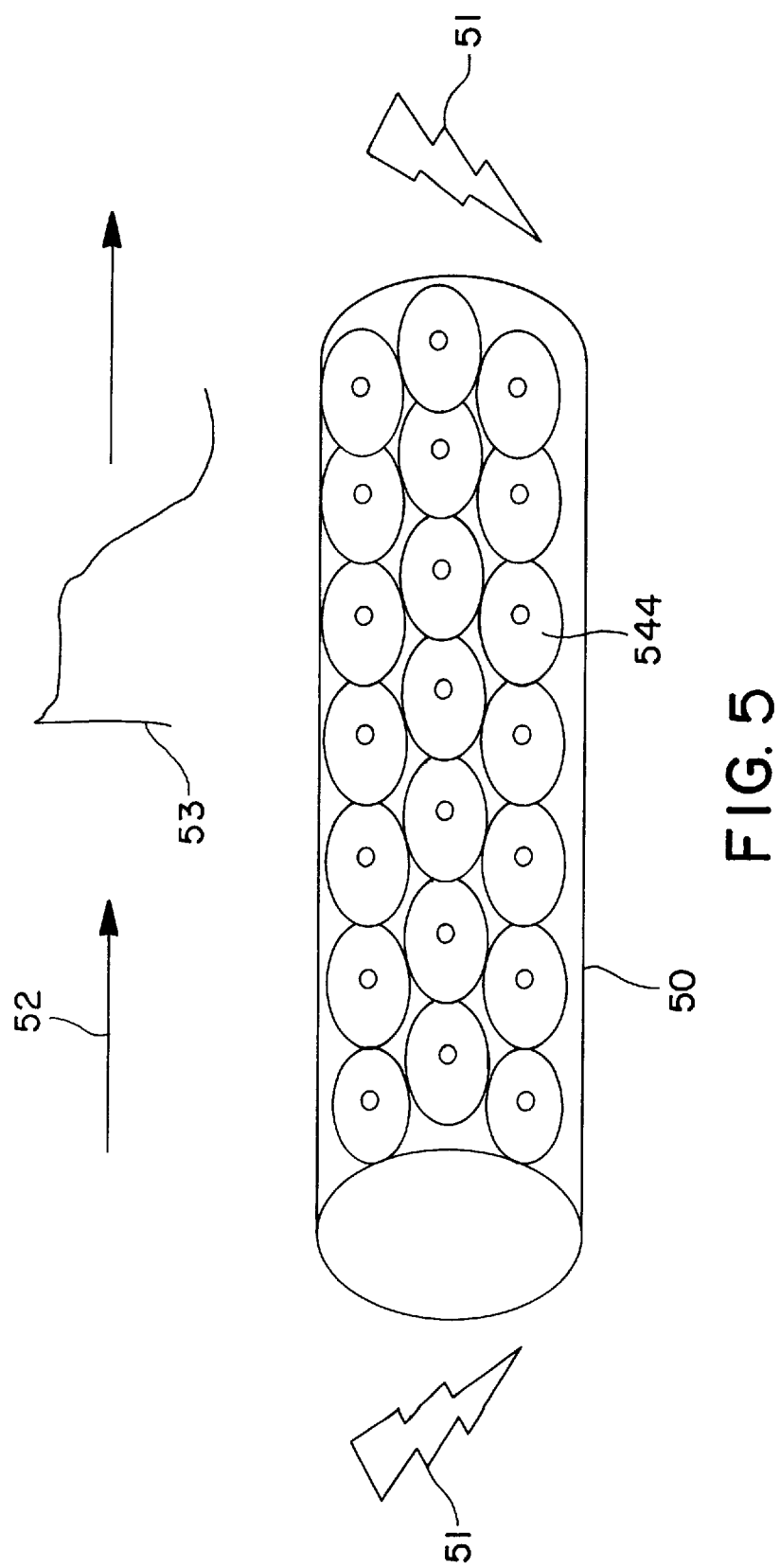
FIG. 5 is a heuristic illustration of a segment of biologic cable and a corresponding wave front propagation.
Figure 6:
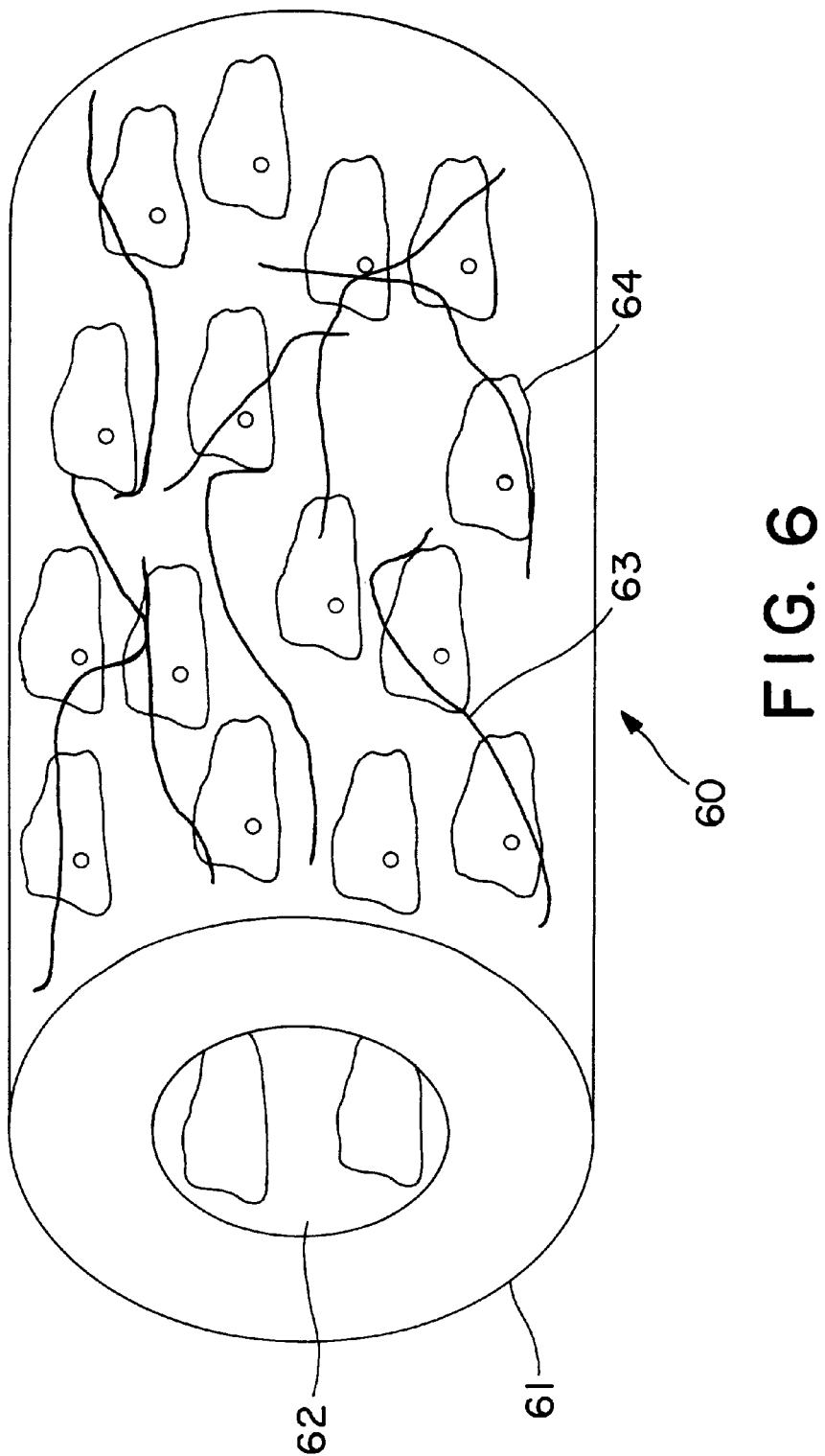
FIG. 6 is a illustration of an insulated biologic cable segment.
Figure 7:
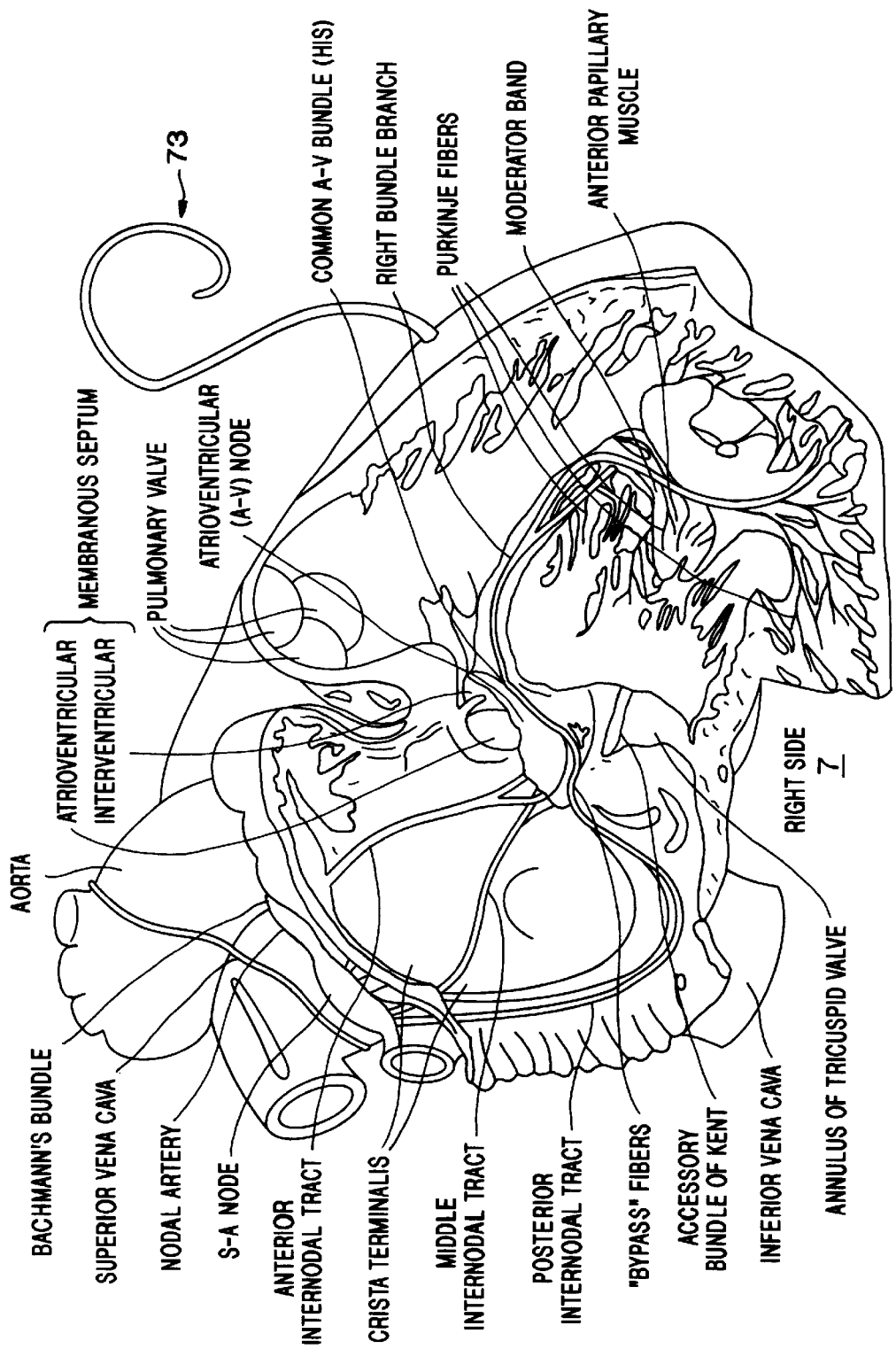
FIG. 7 is a drawing of a heart with a biologic cable extending therefrom.

Referring now to FIG. 5, a segment of biologic cable 50 is illustrated consisting of a number of cells 54, for passing an electrical impulse 51 therethrough. A typical pulsatile impulse moving in direction 52 has a waveform like that illustrated in the changing voltage signal 53. In FIG. 6, a segment of insulated cable 60 is concentric, having an internal segment 62, comprising electrically conductive cells such as the cells from cable 50 in FIG. 5. These are surrounded in a structure of cells 64, trapped by fibrinogen or fibers 62 into a conduit therefor.

Figure 9:
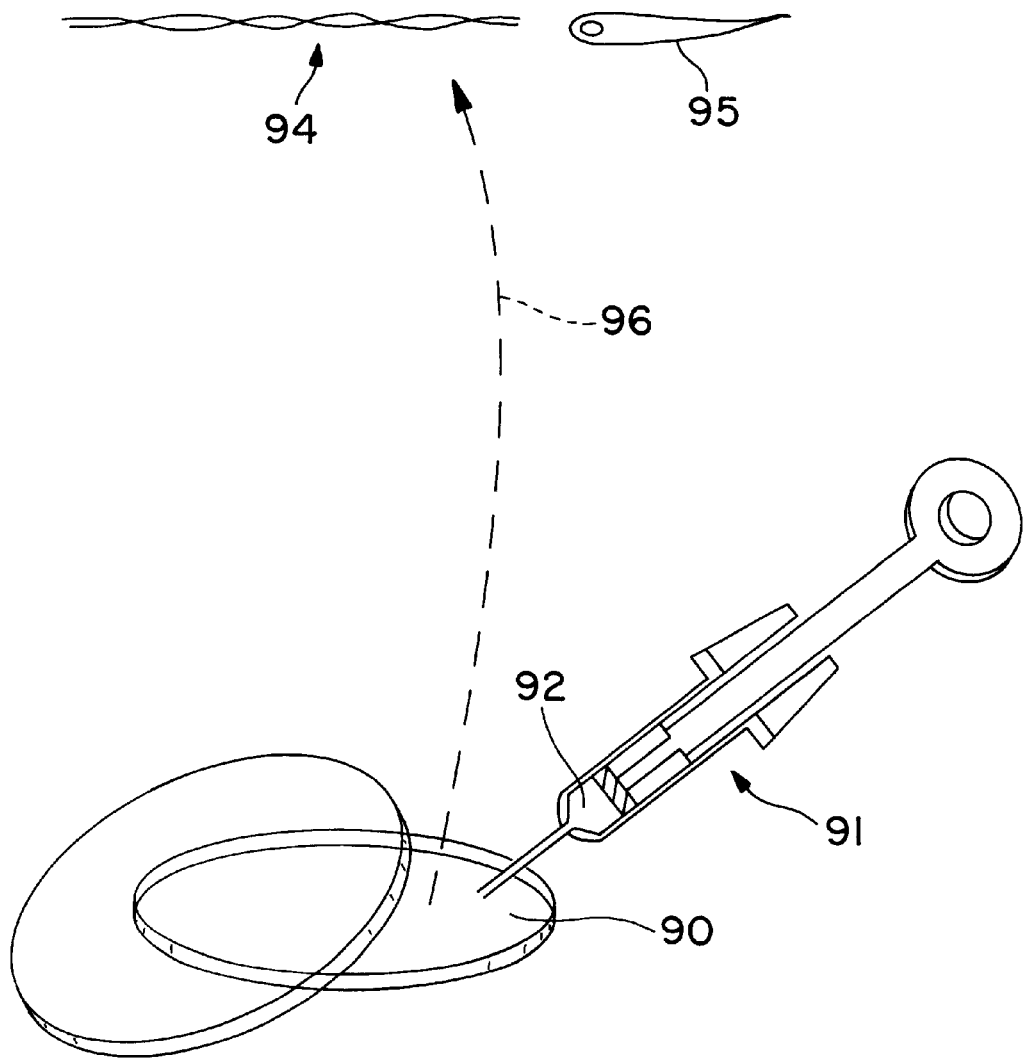
FIG. 9. is an illustration of biologic cable media growing in a dish and a syringe like device for injection.

It should be recognized and many biologic and non active biologic materials could be used to provide both strength and insulation for biologic cables. It is already well understood how to connect living cells to substances as described below with collagen as the preferred substance. By fashioning these substances into cable forms, and doping or seeding them with electrically conductive living cells, preferably cardiomyocetes or but skeletal muscle cells with genetic modification or even neurons can be used, one can form valuable cables with or without external insulative properties. In FIG. 9, a weave of threads 94 can be used to supports autologous genetically transformed cells or selected umbilical or embryonic derived cells and use connected to a needle 95 for facilitating implant into a human or animal. By surgically drawing the treated cable 94 through living tissue, the surgeon can place biologically conductive cells in a cable form in any location within a body; connecting electrically any tissue to any other. The uses can include stimulation of any of these tissues from either implantable devices which initiated electrical stimulus or from already electrically conductive tissue selections nerve and heart tissue which may be connected to one end of the biologic cable.

Also in FIG. 9, the active cellular solution 90 can be drawn into a syringe like device 91 reservoir 92 so as to be later injected into living tissue. By injecting the solution of living cells and withdrawing the surrounding needle from the injection site, a straight biologic cable pathway of living cells for implementing a simple straight length of cable is induced into whatever tissue it is inserted. Trans Myocardial Regenerative techniques may be used if preferred, wherein a laser may poke holes in tissue and a solution of living cells may then be inserted into the hole or hole by a wash or other method.

Cell sources and preparation of materials.

In U.S. Pat. No. 5,602,301 issued to Loren J. Field several example techniques are described in detail of how to generate stable grafts of cells. As Dr. Field explains the process of obtaining appropriate cells for making stable grafts is not difficult. Although by this reference the entire patent is incorporated herein by this reference, it is useful to cite the specific language of column 3 to line 16 of column 4 which describes how one can obtain appropriate cell lines. One would prefer not to use lines derived from tumors, of course since the continued growth into inappropriate areas would be problematic. For cardiac tissue usage, those lines which exhibit the ability to conduct electrical signals would of course be most preferred. One could use embryonic stem cells and using a marker gene with a positive selection scheme select the cells differentiated as needed. Such processing for deriving a particular cell line from a group of stem cells has been defined using marker genes, as in the article by Klug, Soonpaa, Koh and Field, Genetically Selected Cardiomyocytes from Differentiating Embryonic Stem Cells Form Stable Intracardiac Grafts" J.Clin. Invest., V 98, No. 1, July 1996, 216–224. As has also been shown (Soonpaa, et al, Science, (Wash D.C. 1994) N. 264:pages 98–101 Formation of nascent intercalated discs between grafted fetal cardiomyocytes and host myocardium), these cells can make conductive attachments with host myocardial cells, thus being able to deliver the impulse needed to potentially pace a heart, especially where the connection would be make in the Purkinje region as in the FIGS. 1–5 series explained above. Among numerous markers that could be used to select cells that can conduct on e could use the Beta adrenergic "G" proteins identified in "Restoration of B-adrenergic signaling in failing cardiac ventricular myocetes via adenoviral mediated gene transfer, Akhter, et al Proc. National Acad. Sci. USA Vol. 94 pp. 12100–05, Oct. 1997, Medical Sciences. Connexin43 may also be a better marker, since ideotypical Connexin proteins can be identified to differentiate between atrial and ventricular cardiomyocetes. See Transfection of Rhabdomyosarcoma Cells with Connexin43 Induces Myogenic Differentiation (Prolux, et al, Cell Growth and Differentiation Vol. 8, 533–4-, May, 1997; and Disturbed Connexin43 Gap Junction Distribution Correlates with Location of Reentrant Circuits in the Epicardial Border Zone of Healing Canine Infarcts That Cause Ventricular Tachycardia, Circulation, Vol. 95, No. 4, Feb. 18, 1997. See also "Characterization of Gap Junction Channels in Adult Rabbit Atrial and Ventricular Myocardium by Verheule et al, in Circulation Research, Vol. 80, No. 5, May, 1997, 673–681, for more detail on the Connexin proteins and how they may affect conduction.

Alternatively, Autologous cell lines may be used, requiring no immune suppression, starting with harvested muscle cell skeletal myoblasts or undifferentiated stem cells, which are grown to become differentiated cells with marker genes added that include, preferably one or more of the Connexins and a G protein suite, which can be added to an ex-vivo growth of skeletal muscle fibroblasts or satellite cells by any of various gene transfer techniques including those outlined in the cited articles or others as they become available. The most successful would likely be Connexin 43 for enhancing ion conduction with the cardiac tissue into which the cable may later be implanted. Additionally one may simply differentiate the skeletal fibroblasts to myoblasts as is well known, and pace them electrically as is done in the gross surgical procedure of cardiomyoplasty, although in such a procedure the conduction properties may not be as robust.

To select amongst these alternatives consider the advantages and disadvantages of skeletal myoblasts, unbilical cardiac myocetes and embryonic stem cells derived cardiac myocytes. The first class, skeletal myoblasts can be autologous and easy to isolate, especially from younger patients, and provide a good platform for recombinant protein delivery to the myocardium, but they won't couple with cardiac myocytes without genetic modification. Fetal cardiac myocytes are limited currently in their sources and therefore in short supply. They are syngenic and should couple easily with cardiomyocetes, which could cause arrhythmogenic or spurious conduction problems if no insulative layer is interposed between a cable made of them and the patient's heart tissue. More available would be umbilical stem cells from which cardiac myocetes could be derived. While it may be easy to isolate stem cells from this source, purity challenges will have to be met and teratogenic potential is also a possible source of problems.

While collagen preparations are already viable supports for manufacturing biologic cables, the use of carbon fiber matrixies, and even strands of organo-polymers, polyesters and so forth should be considered. Examples of readily available support media include the fibers of collagen that can be woven or spun described in U.S. Pat. Nos. 5,562,946 and 5,709,934 issued to Bell, and Bell and Fofonoff, and the Okano et al articles Hybrid Muscular Tissues: Preparation of Skeletal Muscle Cell—Incorporated Collagen Gels (Cell Transplantation V. 6, No. 2, 109–118, 1997), and Tissue Engineering of Skeletal Muscle, Highly Dense, Highly oriented Hybrid Muscular Tissues Biomicking Native Tissues(ASAIO Journal 1997, 43;M749-M753).

Further, it should be recognized that the embodiments described herein are examples only and that this document's scope is only limited by the following appended claims.

What is claimed is:

1. A method of treatment of heart disease, comprising:
   identifying a first site within a patient's heart from which a desired electrical signal can be obtained;
   identifying a second site within the patient's heart, to which delivery of the electrical signal obtained at the first site is desired;
   coupling the first site to the second site by means of a biologic cable comprising an elongated structure of living cells capable of receiving the electrical signals from the first site, carrying the electrical signals along the length of the elongated structure and delivering said electrical signals to said second site.

2. The method of claim 1 wherein the biologic cable of the coupling step comprises an elongated structure of living cells genetically altered to enhance their conductivity.

3. The method of claim 1 wherein the biologic cable of the coupling step comprises an elongated structure of living skeletal muscle myoblasts genetically altered to enhance their conductivity.

4. The method of claim 1 wherein the biologic cable of the coupling step comprises an elongated structure of living cardiac myoblasts.

5. The method of claims 1 or 2 or 3 or 4 wherein the step of identifying the first site comprises identifying the patient's AV node.

6. The method of claim 5 wherein the step of identifying the second site comprises identifying the patient's His bundle.

7. The method of claim 5 wherein the step of identifying the second site comprises identifying the patient's Purkinje fibers.

8. A method according to claim 1 or claim 2 or claim 3 or claim 4 wherein the step of identifying the second site comprises identifying the patient's His bundle.

9. A method according to claim 1 or claim 2 or claim 3 or claim 4 wherein the step of identifying the second site comprises identifying the patient's Purkinje fibers.

10. A method according to claim 1 or claim 2 or claim 3 or claim 4 wherein the biologic cable of the coupling step comprises an electrode at an end thereof.

11. A method of treatment of heart disease comprising:
    identifying a site within a patient's heart to which delivery of electrical signals is desired;
    coupling the site to an electrical pulse generator by means of a biologic cable comprising an elongated structure of living cells capable of receiving the electrical signals from the electrical pulse generator, carrying the electrical signals along the length of the elongated structure and delivering said electrical signals to the site.

12. A method according to claim 11 wherein the biologic cable of the coupling step comprises an elongated structure of living cells genetically altered to enhance their conductivity.

13. The method of claim 11 wherein the biologic cable of the coupling step comprises an elongated structure of living skeletal muscle myoblasts genetically altered to enhance their conductivity.

14. The method of claim 11 wherein the biologic cable of the coupling step comprises an elongated structure of living cardiac myoblasts.

15. A method according to claim 11 or 12 or 13 or 14 wherein the step of identifying said site within said patient's heart comprises identifying said patients His bundle.

16. The method of claim 11 or 12 or 13 or 14 wherein said step of identifying said site within said patient's heart comprises identifying said patient's Purkinje fibers.

17. The method of claim 11 or 12 or 13 or 14 wherein the biologic cable of the coupling step comprises an electrode at an end thereof.

* * * * *